United States Patent
Steffan

(10) Patent No.: US 12,042,199 B2
(45) Date of Patent: Jul. 23, 2024

(54) APPARATUS FOR REMOVAL OF FIXATION MEMBERS

(71) Applicant: Howmedica Osteonics Corp., Mahwah, NJ (US)

(72) Inventor: Elena Steffan, Sleepy Hollow, NY (US)

(73) Assignee: Howmedica Osteonics Corp., Mahwah, NJ (US)

(*) Notice: Subject to any disclaimer, the term of this patent is extended or adjusted under 35 U.S.C. 154(b) by 414 days.

(21) Appl. No.: 17/332,050

(22) Filed: May 27, 2021

(65) Prior Publication Data

US 2022/0378489 A1 Dec. 1, 2022

(51) Int. Cl.
  *A61B 17/92* (2006.01)
  *A61B 17/84* (2006.01)

(52) U.S. Cl.
  CPC ............ *A61B 17/92* (2013.01); *A61B 17/846* (2013.01)

(58) Field of Classification Search
  CPC .......... A61B 17/92; B25C 11/02; B25C 11/00
  See application file for complete search history.

(56) References Cited

U.S. PATENT DOCUMENTS

| | | | |
|---|---|---|---|
| 1,445,514 A * | 2/1923 | Johnson | B25C 11/00 254/21 |
| 1,454,239 A * | 5/1923 | Kawamura | B25C 11/00 254/25 |
| 1,550,894 A * | 8/1925 | Erickson | B25F 1/006 7/105 |
| 4,227,730 A * | 10/1980 | Alexander | A61B 17/122 294/131 |
| 6,066,143 A * | 5/2000 | Lane | A61B 17/92 606/205 |
| 6,886,810 B2 * | 5/2005 | Forrester | B25C 11/00 254/22 |
| 7,189,243 B1 * | 3/2007 | Seelig | A61B 17/92 606/104 |
| 7,438,279 B2 | 10/2008 | Eby et al. | |
| 7,506,908 B2 * | 3/2009 | Metcalfe | B25B 7/02 606/104 |
| D642,678 S * | 8/2011 | Dockstader | D24/133 |
| D768,855 S * | 10/2016 | McMillan | D24/143 |
| D796,039 S * | 8/2017 | McMillan | D24/143 |
| 9,750,554 B2 * | 9/2017 | Lee | A61B 17/92 |
| 10,099,358 B2 * | 10/2018 | McMillan | B25C 11/00 |
| 2002/0099309 A1 * | 7/2002 | Beger | A61B 17/1697 600/585 |
| 2005/0062026 A1 * | 3/2005 | Holcomb | B25C 11/00 254/25 |
| 2010/0087831 A1 | 4/2010 | Marx | |
| 2010/0234851 A1 * | 9/2010 | Graves | A61B 17/92 29/268 |
| 2011/0000090 A1 * | 1/2011 | Pau | A47J 43/26 30/120.2 |

* cited by examiner

Primary Examiner — David W Bates
(74) Attorney, Agent, or Firm — Lerner David LLP

(57) ABSTRACT

A pin removal tool includes a first arm member and a second arm member opposing the first arm member and connected to the first arm member at a pivot axis. The first and second arm members form a first interface therebetween at a first end of the tool configured to remove a headless pin and a second interface therebetween at a second end of the tool configured to remove a headed pin.

13 Claims, 3 Drawing Sheets

US 12,042,199 B2

APPARATUS FOR REMOVAL OF FIXATION MEMBERS

BACKGROUND OF THE INVENTION

Orthopedic surgery often requires the use of guides and other devices that are temporarily affixed to one or more bone. These devices can be affixed using a variety of means, one of which is a pin. Pins can also be used to temporarily hold bone pieces together until the bones either fuse or a more permanent means is implemented. Pins typically have a shaft or shank and may or may not include a head at the end of the shaft.

Once a pin is no longer needed, it may be removed. Pins, which are driven in a manner similar to nails, are firmly held in the bone. Thus, a substantial amount of force may be needed to remove a pin. However, pins must be removed without damaging the pins, any device the pin is being used to secure, and the underlying bone. Equipping the pins with heads offers a gripping surface to aid in pin removal, however, an assortment of pins may be included in a single surgery, in which some pins may be equipped with heads and some pins may be headless. Separate devices may then be needed for removing headed and headless pins. Thus, multiple tools may be brought into the surgical room just to handle pin removal. This may unnecessarily clutter the operating theatre and require the surgeon to switch back and forth between tools when removing the different types of pins. Overcrowding of equipment and alternating between tools may reduce efficiency and hinder performance during surgery. It may also increase the risk for infection.

Thus, further improvements to the design of a pin removal tool to effectively remove headed and headless pins while reducing the congestion of surgical tools are therefore desired.

BRIEF SUMMARY OF THE INVENTION

The present disclosure describes a tool useful for the engagement with and the removal of various types of fixation elements, such as pins. The tool is configured to have multiple engagement interfaces for engaging with different types of fixation devices. For example, a first portion or end of the tool may be configured to engage with and grasp a headed pin, and a second portion or end of the tool may be configured to engage with and grasp a headless pin. The advantages of the tool at least include the capability of grasping different types of fixation elements with a single tool, which may improve ease and efficiency of performing different tasks (e.g., removing headed and headless pins), particularly in the surgical process, and may also reduce the clutter of carrying separate tools to perform the different tasks.

In certain preferred embodiments, a pin removal tool may include a first arm member, and a second arm member opposing the first arm member and connected to the first arm member at a pivot axis, wherein the first and second arm members form a first interface therebetween at a first end of the tool configured to remove a headless pin and a second interface therebetween at a second end of the tool configured to remove a headed pin. The first and second arm members may be elongate and the first and second interfaces may be located at opposing ends of the arm members. The first interface may be located closer to the pivot axis than the second interface. Rotation of the arms about the pivot axis from a first position to a second position may clamp a fixation element between the arms at one of the first and second interfaces. The first interface may include a cam member and a clamp surface opposed the cam member. A transition from the first position to the second position may move a cam surface of the cam member closer to the clamp surface to trap a headless pin therebetween. The second interface may include a first recess and a second recess in communication with the first recess. The first recess may have a larger cross-section than the second recess. The first recess may be configured to receive the head of a pin. The second recess may be configured to receive the shank of a pin. The first and second recesses may be formed at least partially by each of the first and second arm members, the arm members contouring the fixation element in the second position.

The tool may be biased to remain in the first position when no external force is applied to the tool. The first arm member may include a latch configured to couple to a protrusion extending from the second arm member to lock the tool in the second position. Rotation of the arms about the pivot axis from a first position to a second position may close the first interface at the first end and open the second interface at the second end. The pivot axis may be located substantially in the middle of the first and second ends. The first and second arms may be contoured to fit fingers of a user for enhanced grip. The first arm may be arcuate in a first direction and the second arm may be arcuate a second direction opposite the first direction.

In other aspects of the disclosure, a pin removal tool may include a first arm member, and a second arm member opposing the first arm member and connected to the first arm member at a pivot axis, wherein the first and second arm members form a first interface therebetween configured to engage and remove a headless pin for removal and a second interface therebetween configured to engage a headed pin for removal. The first and second arms may extend from a first end to a second end, and the first interface may be disposed at either the first or second end. The second interface may be disposed at an end opposite that of the first interface and the pivot axis may be located closer to the first end than the second end.

DETAILED DESCRIPTION

The present disclosure will now be described more fully hereinafter with reference to the accompanying drawings, in which some, but not all aspects of the disclosure are shown. Indeed, the disclosure may be embodied in many different forms and should not be construed as being limited to the aspects set forth herein. Like reference numbers refer to like elements throughout. As used herein, the terms "substantially," "generally," "approximately," and "about" are intended to mean that slight deviations from absolute are included within the scope of the term so modified. Examples of a tool disclosed herein may be described in the context of removing pins from a bone, however, it should be understood that the tool may be used for gripping or removing any fixation or elongate member, such as a nail, a screw, or the like.

Figure 1:
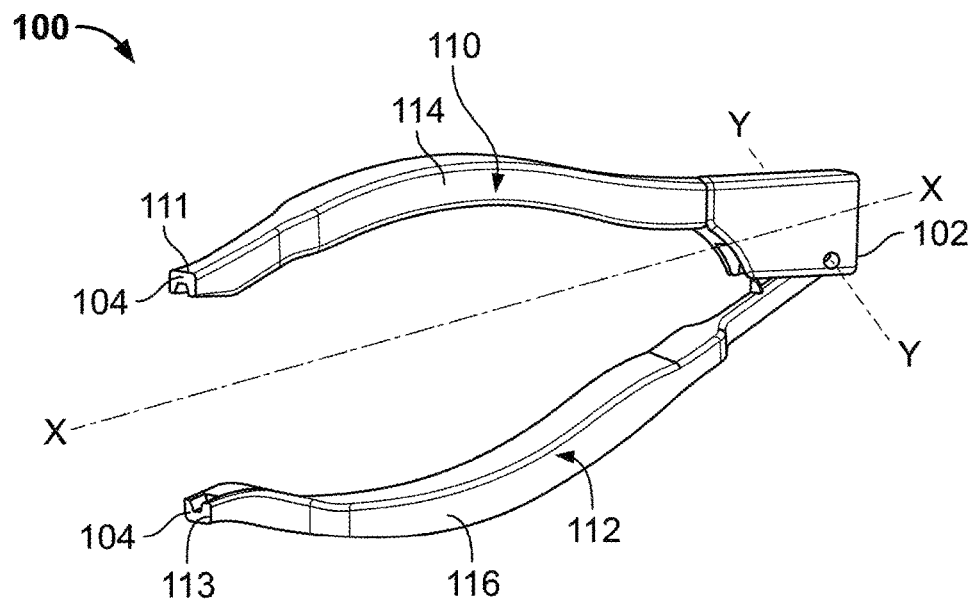
FIG. 1 is a perspective view of a pin removal tool in an open configuration according to an embodiment of the disclosure.

FIG. 1 illustrates a pin removal tool 100 in a first position, or an open configuration, according to an embodiment of the present disclosure. Pin removal tool 100 includes a first upper arm member 110 pivotably coupled to a second lower arm member 112. Both arm members extend between a first end 102 and a second end 104 of the tool 100. Upper arm member 110 is coupled to lower arm member 112 proximate to first end 102 such that the arm members pivot with respect to each other about pivot axis Y. From first end 102, arm members 110, 112 may be elongate extending generally along longitudinal axis X. In the open configuration, as shown in FIG. 1, first arm member 110 has a free end 111 and second arm member 112 has free end 113 at second end 104.

Figure 2:
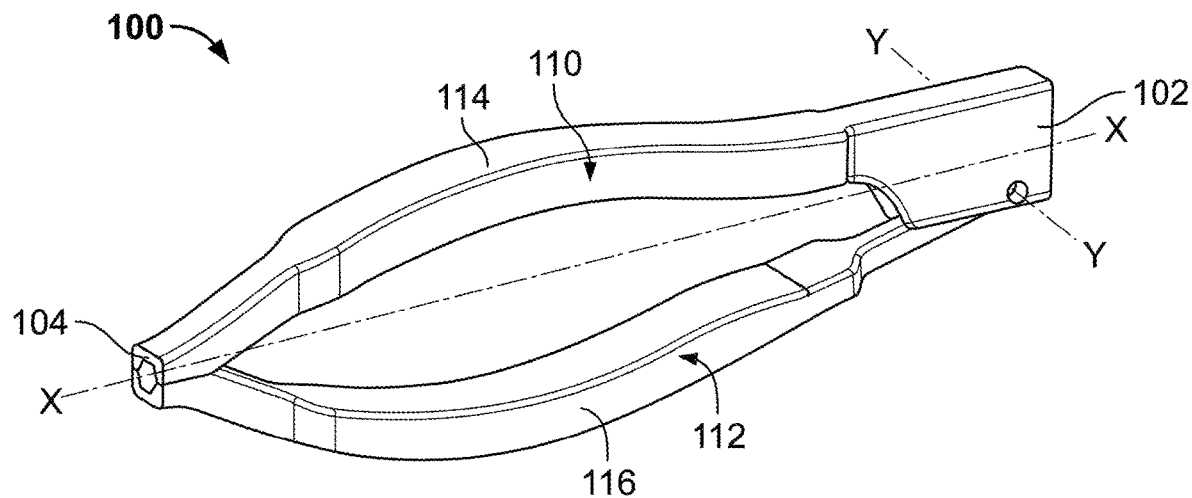
FIG. 2 is a perspective view of the pin removal tool of FIG. 1 in a closed configuration.
Figure 3:
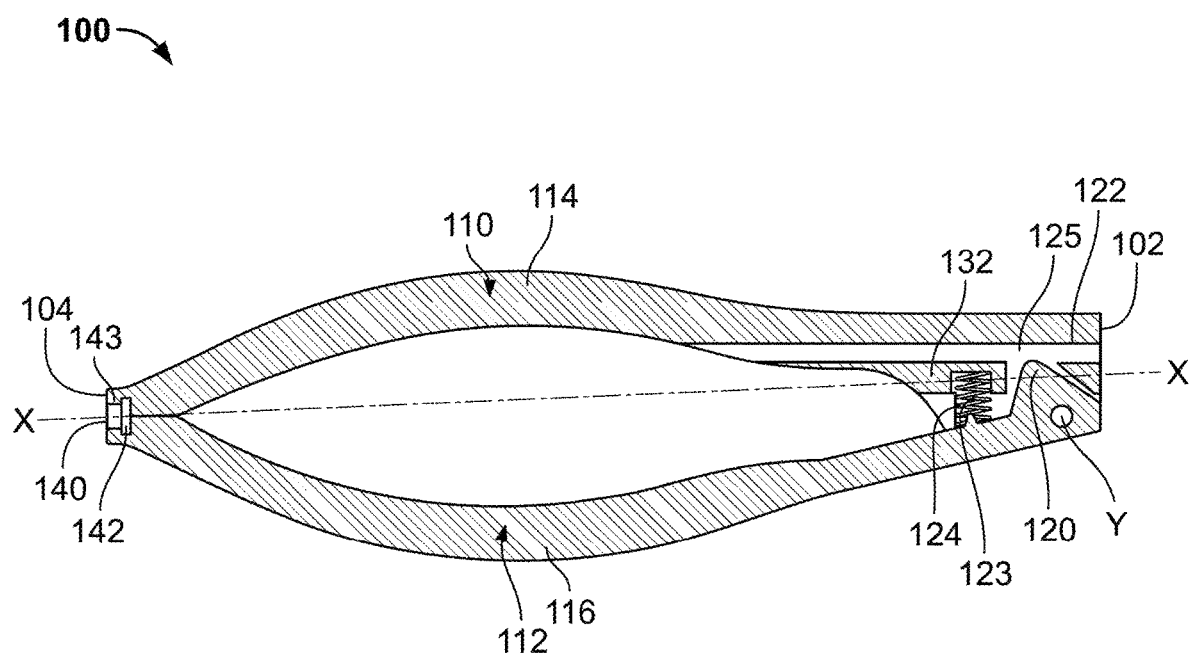
FIG. 3 is a cross-sectional side view of the pin removal tool of FIG. 2.

Each arm member 110, 112 may have a gripping portion 114, 116, respectively, which are generally arcuate. That is, as the arm members extend from first end 102 to second end 104, the arm members also extend in a direction away from longitudinal axis X (and away from each other) and continue to extend back toward longitudinal axis X (and each other) to form a convex gripping portion, as shown in FIG. 1. Convex gripping portions 114, 116 may improve a user's grip around pin removal tool 100 to increase stability and accuracy while wielding the tool. Gripping portions 114, 116 may have a contoured shape (or include an attachment) defining recesses sized to comfortably receive the fingers of a user. For example, upper arm member 110 may have a single larger recess sized to fit the palm of the user, and lower arm member 112 may have four smaller recesses sized to fit the fingers of the user. It is contemplated that gripping portions 114, 116 may have a greater width and/or thickness than the portions of arm members 110, 112 surrounding the gripping portions (i.e., the portions of the arm members more proximate to first end 102 and second end 104 relative to the gripping portions) wherein the width is defined in the direction parallel to pivot axis Y, and the thickness is defined in a direction generally perpendicular to longitudinal axis X and pivot axis Y. Each arm member 110, 112 may have substantially similar lengths as shown in FIGS. 1-3, however, it is contemplated that one arm member may have a length greater than the other arm member. For example, one arm member may extend farther than the other arm member at the first and/or second ends such that the pin is clamped between an end of one arm member and a surface of the other arm member between the first and second ends. While arm members are preferably convex in shape, as depicted, it should be understood that arm members 110, 112 can have other configurations that are not convex. For example, arm members may each extend straight along an axis. Alternatively, one arm member may be straight while the other may be convex.

In the open configuration shown in FIG. 1, upper arm member 110 is coupled to lower arm member 112 at first end 102, while the arm members are separated at second end 104 so as to define a gap or a distance between free end 111 of upper arm member 110 and free end 113 of lower arm member 112. Pin removal tool 100 may be biased in the open configuration such that the tool remains in the open configuration while at rest. Such biasing may be done by a spring 124, for example, which may wrap around a protrusion 123 extending from the surface of lower arm member 112 toward upper arm member 110. The spring 124 is sized to contact a surface of upper arm member 110 or a secondary arm 132 extending along upper arm member 110 and apply a biasing force to separate the arm members 110, 112 when the tool 100 is in or near a closed configuration. Pin removal tool 100 is illustrated in FIG. 2 in a second position, also referred to as the closed or compressed configuration. That is, upper arm member 110 is still coupled to lower arm member 112 at first end 102 while free end 111 of upper arm member 110 contacts free end 113 of lower arm member 112. Pin removal tool 100 may be actuated from the open configuration to the closed configuration by applying an inward force (i.e., toward longitudinal axis X) upon one or both arm members 110, 112 anywhere along the length of the arm members. For example, a user may wrap one hand around pin removal tool 100 by pressing the palm of the hand against gripping portion 114 of upper arm member 110 and wrapping the fingers of the same hand around gripping portion 116 of lower arm member 112 to squeeze and apply a compressive force to each arm member 110, 112. Pin removal tool 100 may be used to remove a pin or pins which may be temporarily inserted into a patient, particularly the bone of patient, during surgery. Both first end 102 and second end 104 may be used for pin removal, and pin removal tool 100 may be used to remove a headed or headless pin, as discussed below in greater detail.

FIG. 3 is a cross-sectional view of pin removal tool 100 showing components of the tool used for gripping and/or extracting fixation members. In some examples, first end 102 of pin removal tool 100 has an interface between upper arm member 110 and lower arm member 112 for gripping headless pins. For instance, upper arm member 110 includes an opening 125 that extends through a portion of upper arm member 110. The opening is sized and shaped to receive an elongate member such as a pin. The pin is inserted into opening 125 by positioning the tool over the pin when pin removal tool 100 is in the open configuration shown in FIG. 1. After the pin is inserted, lower arm member 112 is rotated about pivot axis Y relative to upper arm member 110 to transition pin removal tool 100 from the open configuration to the closed configuration shown in FIGS. 2 and 3. When pin removal tool 100 reaches the closed configuration, or substantially near the closed configuration, a surface of cam member 120 contacts the headless pin and traps the pin between cam member 120 and opposing clamping surface 122. The compressive force applied by the user to arm members 110, 112 is applied directly to the headless pin via cam member 130. The pin may be inserted all the way through opening 125, and it should be understood that the pin must be inserted into opening 125 at least a minimum distance to be contacted by cam member 120. Upper arm member 110 may contact lower arm member 112 at the second end 104 to absorb the force of compression to reduce or prevent over-compression of the arm members 110, 112 against a pin positioned within the first end 102 of the tool 100, or when there is no pin positioned between the arm members 110, 112. Upper arm member 110 further includes an arm 132 which is sized and shaped to engage a stop such as protrusion 123 on lower arm member 112. In some examples, the arm 132 may contact and compress the spring 124 with a force sufficient to engage the protrusion 123 and absorb the force of compression to reduce or prevent over-compression of the arm members 110, 112 against a pin positioned within the first end 102 or the second end 104 of the tool 100. The arm 132 may also engage the protrusion 123 to prevent over-compression of the arm members 110, 112 when there is no pin positioned between the arm members.

In some examples, second end 104 of pin removal tool 100 may be used to grip and/or extract headed pins. Second end 104 includes an interface between upper arm member 110 and lower arm member 112 wherein, in the closed configuration, upper and lower arm members 110, 112 define a first recess 140 and a second recess 142 in communication with each other. First recess 140 has a generally circular cross-section having a first radius, and second recess 142 has a generally circular cross-section that has a second radius greater than the first radius. First and second recesses 140, 142 may be symmetric along longitudinal axis X, such that upper arm member 110 and lower arm member 112 each define at least a portion of the recesses 140, 142. Second recess 142 is sized and shaped to receive and contour the head of a pin, and first recess 140 is sized and shaped to receive and contour the shank of the pin. It is also contemplated that first recess 140 and/or second recess 142 may be defined substantially or completely by one of upper arm member 110 or lower arm member 112.

As noted above, second end 104 of pin removal tool 110 may be used to grip and/or remove headed pins, nails, or the like. Beginning with pin removal tool 100 at least partially in an open configuration as shown in FIG. 1, second end 104 may be positioned over the head of a headed pin. A user may then squeeze or compress pin removal tool 100 to transition the tool from the open configuration to the closed configuration shown in FIGS. 2-3 such that the shank and head of the pin are received by first and second recesses 140, 142, respectively. In other words, after the user has actuated pin removal tool 100 to rotate upper arm member 110 with respect to lower arm member 112 so that tool 100 is in a substantially or completely closed configuration, the head of a pin may be positioned within second recess 142 and the shank of the pin may be positioned within first recess 140. From there, the user may apply a force along longitudinal axis X to remove the pin from a bone. Generally, longitudinal axis X may be collinear with the axis of the shank of the pin, and the force may be applied in the direction opposite the object in which the pin is inserted. A lip 143 or ledge is formed by the difference in radii between first recess 140 and second recess 142. When pin removal tool 100 is in the closed configuration positioned over the head of a pin, the force applied by the user is transferred to the head of the pin by lip 143 to extract the pin from the bone. It is contemplated that the user may apply a force in a direction transverse to longitudinal axis X. For example, the user may apply a force at a first angle relative to longitudinal axis X to loosen the pin from its hold in the bone, and further apply a force at an angle opposite the first angle relative to longitudinal axis X to continue loosening the pin. It is also contemplated that if the force applied by the user via pin removal tool 100 causes the head of the pin to separate from the shank of the pin while at least a portion of the shank remains in the bone, first end 102 of pin removal tool 100 may be used in the manner described above to remove the shank portion left in the bone.

Figure 4:
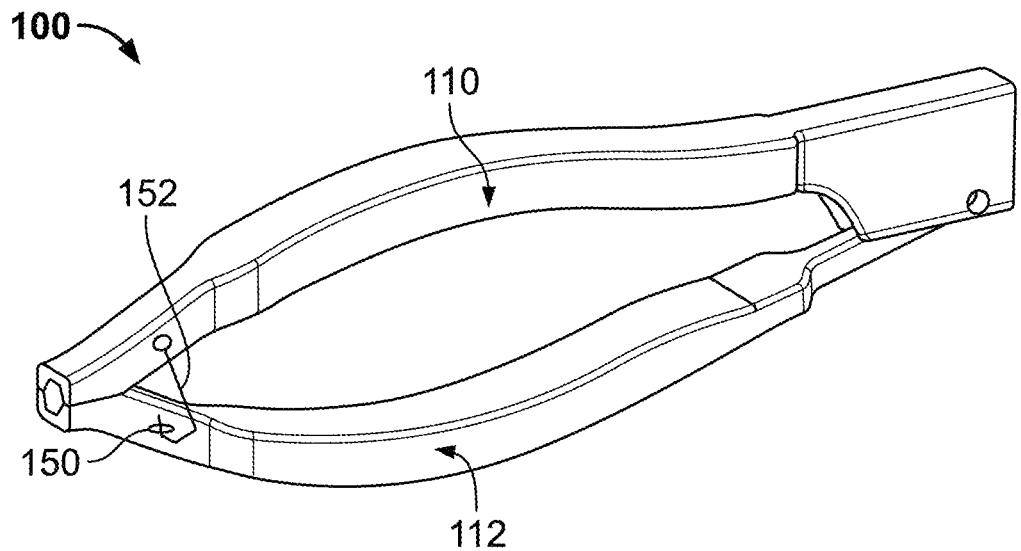
FIG. 4 is a perspective view of a pin removal tool according to another embodiment of the disclosure.

In some examples, pin removal tool 100 may include a protrusion 150 or a loop defining an eyelet on one of the arm members, e.g., lower arm member 112, and pin removal tool 100 may include a latch 152 or hook pivotably coupled to the other arm member, e.g., upper arm member 110, as shown in FIG. 4. When pin removal tool 100 is in the closed configuration, latch 152 and protrusion 150 may be positioned on the tool such that latch 152 may pivot or rotate with respect to upper arm member 110 to engage with protrusion 150 of lower arm member 112 to lock pin removal tool 100 in the closed configuration. In the locked condition, latch 152 may prevent pin removal tool 100 from transitioning to the open configuration whether the pin removal tool is biased in the open configuration or the user applies a force to open the pin removal tool. The user may manually disengage latch 152 from protrusion 150 to transition pin removal tool 100 into an unlocked condition and subsequently transition the pin removal tool to the open configuration.

Figure 5:
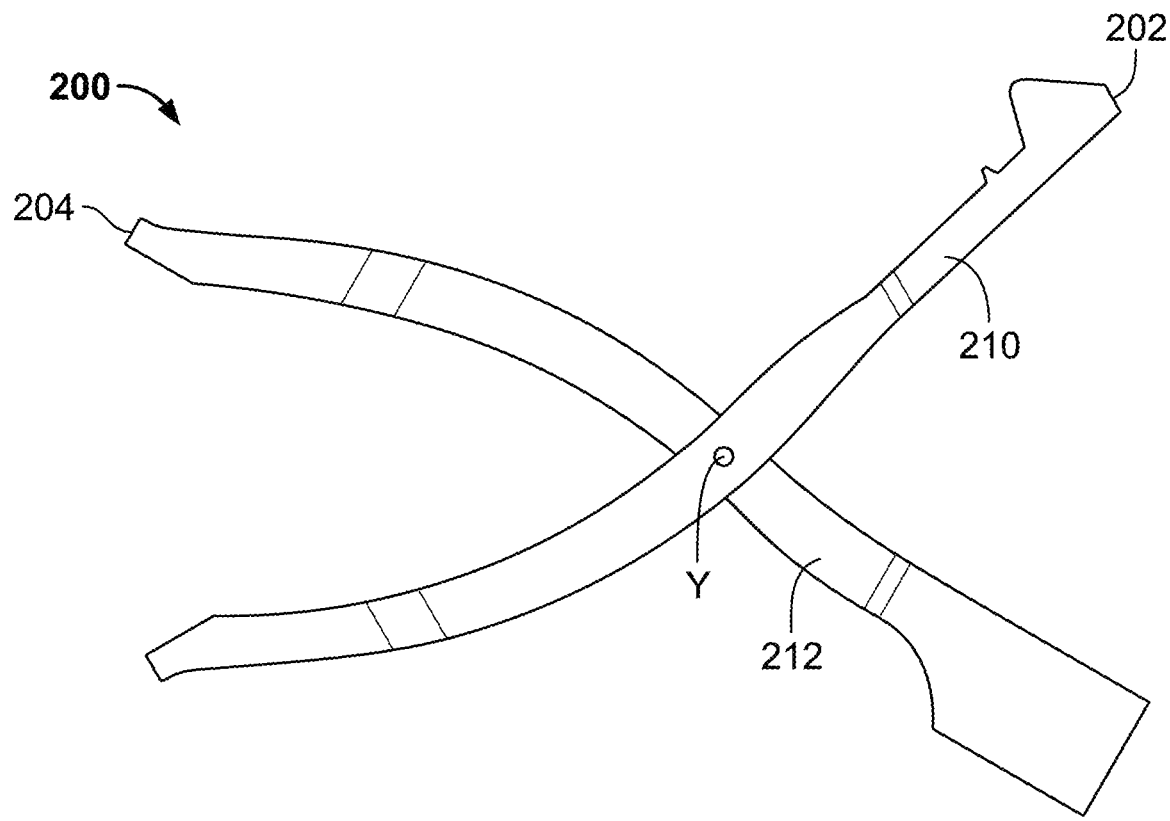
FIG. 5 is a schematic view of a pin removal tool according to another embodiment of the disclosure.

In some examples, the arm members may be pivotably coupled generally in the middle of the arm members such that the pivot axis is located generally in the middle of the first and second ends of the tool. For example, FIG. 5 illustrates pin removal tool 200 having a first arm member 210 and a second arm member 212 which rotate with respect to each other generally about the middle points of each arm member at pivot axis Y such that when one end, e.g, first end 202, is actuated to the closed condition as described above, the opposite end e.g., second end 204, is actuated to the open configuration, and vice versa. It is also contemplated that the arm members may be pivotably coupled to each other at any location between their middle portions and either the first or second end, in which the rotation of the arm members will be substantially similar to the example shown in FIG. 5. For example, the pivot axis may be generally in the middle of the arm members, but closer to the first end than the second end.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pin removal tool comprising:
a first arm member; and
a second arm member opposing the first arm member and connected to the first arm member at a pivot axis,
wherein the first and second arm members form a first interface therebetween at a first end of the tool configured to remove a headless pin and a second interface therebetween at a second end of the tool configured to remove a headed pin,
wherein the pivot axis is positioned at the first end of the tool,
Wherein the second interface of the tool defines a recess configured to the headed pin,
wherein the first and second arm members are configured to be rotated about the pivot axis from a first position to a second position to clamp one of the headless pin or the headed pin between the first and second arm members at one of the first and second interfaces,
wherein the recess includes a first recess and a second recess in communication with the first recess, and
wherein the first and second recesses are formed at least partially by each of the first and second arm members, the first and second arm members shaped to match a contour of a head and shaft of the headed pin in the second position.

2. The pin removal tool of claim 1, wherein the first and second arm members are elongate and the first and second interfaces are located at opposing ends of the arm members.

3. The pin removal tool of claim 1, wherein the first interface is located closer to the pivot axis than the second interface.

4. The pin removal tool of claim 1, wherein the first interface includes a cam member and a clamp surface opposing the cam member.

5. The pin removal tool of claim 4, wherein a transition from the first position to the second position moves a cam surface of the cam member closer to the clamp surface to trap the headless pin therebetween.

6. The pin removal tool of claim 1, wherein the first recess has a larger cross-section than the second recess.

7. The pin removal tool of claim 1, wherein the first recess is configured to receive the head of the headed pin.

8. The pin removal tool of claim 1, wherein the second recess is configured to receive the shank of the headed pin.

9. The pin removal tool of claim 1, wherein the tool is biased to remain in the first position when no external force is applied to the tool.

10. The pin removal tool of claim 1, wherein the first arm member includes a latch configured to couple to a protrusion extending from the second arm member to lock the tool in the second position.

11. The pin removal tool of claim 1, wherein the first and second arm members are configured to be rotated about the pivot axis from the first position to the second position to close the first interface at the first end and the second interface at the second end.

12. The pin removal tool of claim 1, wherein the first and second arm members are contoured to fit fingers of a user for enhanced grip.

13. The pin removal tool of claim 1, wherein the first arm member is arcuate in a first direction and the second arm member is arcuate a second direction opposite the first direction.

* * * * *